US005973153A

United States Patent [19]
Adaway et al.

[11] Patent Number: 5,973,153

[45] Date of Patent: Oct. 26, 1999

[54] PROCESS FOR THE PREPARATION OF HALO-4-PHENOXYQUINOLINES

[76] Inventors: Tim J. Adaway, 3117 Lambros Dr., Midland, Mich. 48642; Jeff T. Budd, 1341 Chrismill La., Mount Pleasant, S.C. 29464; Ian R. King, 80 rue de la Paix, Schwenheim, France, 67440; Karl L. Krumel, 614 Shorefront Cir., Midland, Mich. 48640; Larry D. Kershner, 810 Stillmeadow La.; Julie L. Maurer, 4381 Monroe Rd., both of Midland, Mich. 48642; Thomas A. Olmstead, 7423 Park Village Rd., San Diego, Calif. 92129; Gary A. Roth, 1250 E. Stewart Rd., Midland, Mich. 48640; Jimmy J. Tai, 311 Seminole Ct., Midland, Mich. 48642; Mark A. Hadd, 15 Swampscott Ave., Peabody, Mass. 01960

[21] Appl. No.: 09/007,429

[22] Filed: Jan. 15, 1998

Related U.S. Application Data

[60] Provisional application No. 60/036,623, Jan. 31, 1997.

[51] Int. Cl.[6] .......... C07D 215/16

[52] U.S. Cl. .......... 546/153

[58] Field of Search .......... 546/153

[56] References Cited

U.S. PATENT DOCUMENTS

| | | | |
|---|---|---|---|
| 5,145,843 | 9/1992 | Arnold et al. | 514/63 |
| 5,245,036 | 9/1993 | Robey et al. | 546/153 |

FOREIGN PATENT DOCUMENTS

| | | |
|---|---|---|
| 7731 | 3/1970 | France . |
| 685560 | 8/1995 | Switzerland . |

OTHER PUBLICATIONS

Chemical Abstracts 124:29619, Yoshizawa, abstract of WO 9523787, 1995.

Chemical Abstracts 124:55810, Macquarrie, abstract of CH 685560, 1995.

Chemical Abstracts 121:205192, Prakash, abstract of Tetrahedron Letters, 35(24), pp. 4211–4214, 1994.

R. G. Gould, Jr. et al., *J. American Chemical Soc.,* 61, 2890 (1939).

C. C. Price et al., *Organic Synthesis Collective vol. 3,* pp. 272–275.

T. R. Kelly et al., *Tetrahedron,* 41, 3033–3036 (1985).

M. Nasa et al., Kokai Patent No. Hei 5(1993)–155858, published Jun. 22, 1993 (translation).

J. Chattopadhyay et al., *Indian Journal of Chemistry,* 29B, 98–100 (1990).

C. C. Price et al., *J. American Chemical Soc.,* 68, 1204–1208 (1946).

A. J. Lin et al., *J. Medicinal Chemistry,* 21, 268–271 (1978).

H. Yoshizawa, PCT Patent Application WO 9523787, published Sep. 8, 1995 (abstract).

O. Prakash et al., *Tetrahedron Letters,* 35, 4211–4214 (1994).

Fortunak, et al; Preparation of Mappicine Ketones from Camptothecins: Chemistry of te Camptothecin E Ring; *Tetrahedron Letters,* vol. 35, No. 32, pp. 5763–5764, 1994.

*Primary Examiner*—D. Margaret M. Mach
*Attorney, Agent, or Firm*—Craig E. Mixan; D. Wendell Osborne

[57] ABSTRACT

The present invention relates to a new improved, simplified process for the preparation of halo-4-phenoxyquinolines, whereby thionyl chloride is used as the chlorinating agent to prepare the corresponding chloroquinoline intermediate prior to the final coupling reaction, and a single, inert high boiling polyether solvent is used throughout the entire reaction procedure.

6 Claims, No Drawings

PROCESS FOR THE PREPARATION OF HALO-4-PHENOXYQUINOLINES

RELATED APPLICATIONS

This application claims the benefit of U.S. Provisional Application No. 60/036,623, filed Jan. 31, 1997.

FIELD OF THE INVENTION

The present invention relates to a new improved, simplified process for the preparation of halo-4-phenoxyquinolines, whereby thionyl chloride is used as the chlorinating agent to prepare the corresponding chloroquinoline intermediate prior to the final coupling reaction, and a single, inert high boiling polyether solvent is used throughout the entire reaction procedure.

BACKGROUND OF THE INVENTION

U.S. Pat. No. 5,145,843 describes halo-4-phenoxyquinoline compounds as having excellent plant fungicide activity, such as those of formula (1), (1)

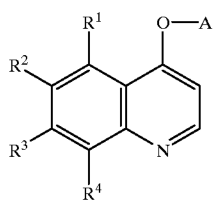

wherein $R^1$ and $R^3$ are independently halo and $R^2$ and $R^4$ are H; or $R^3$ is halo, $R^1$ is halo or H, and $R^2$ and $R^4$ are H; or $R^4$ is halo and $R^1$ to $R^3$ are H;

A is a phenyl group of formula (2)

(2)

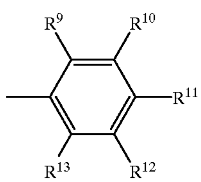

wherein $R^9$ to $R^{13}$ are independently H, CN, $NO_2$, OH, halo, $(C_1-C_4)$alkyl, $(C_2-C_4)$alkanoyl, halo$(C_1-C_7)$alkyl, hydroxy $(C_1-C_7)$alkyl, $(C_1-C_7)$alkoxy, halo$(C_1-C_7)$alkoxy, $(C_1-C_7)$ alkylthio, halo$(C_1-C_7)$alkylthio, phenyl, substituted phenyl, phenoxy, substituted phenoxy, phenylthio, substituted phenylthio, phenyl$(C_1-C_4)$alkyl, substituted phenyl$(C_1-C_4)$ alkyl, benzoyl, $SiR^{20}R^{21}R^{22}$, or $OSiR^{20}R^{21}R^{22}$ where $R^{20}$, $R^{21}$, and $R^{22}$ are H, a $(C_1-C_6)$alkyl group, phenyl, or substituted phenyl, provided that at least one of $R^{20}$, $R^{21}$, and $R^{22}$ is other than H, or $R^{11}$ and $R^{12}$ or $R^{12}$ and $R^{13}$ combine to form a carbocyclic ring, and provided that unless all of $R^9$ to $R^{13}$ are H or F, then at least two of $R^9$ to $R^{13}$ are H.

Wherein the foregoing definitions, the term substituted phenyl refers to phenyl substituted with up to three groups selected from halo, $(C_1-C_{10})$alkyl, halo$(C_1-C_7)$alkyl, hydroxy$(C_1-C_7)$alkyl, $(C_1-C_7)$alkoxy, halo$(C_1-C_7)$alkoxy, phenoxy, phenyl, $NO_2$, OH, CN, $(C_1-C_4)$alkanoyloxy, or benzyloxy.

The term alkyl refers to linear, branched, or cyclic alkyl.

The term halo refers to fluoro, chloro, bromo, or iodo.

The term substituted phenoxy refers to a phenoxy group substituted with up to three groups selected from halo, $(C_1-C_{10})$alkyl, halo$(C_1-C_7)$alkyl, hydroxy-$(C_1-C_7)$alkyl, $(C_1-C_7)$alkoxy, halo$(C_1-C_7)$alkoxy, phenoxy, phenyl, $NO_2$, OH, CN, $(C_1-C_4)$alkanoyloxy, or benzyloxy.

The term substituted phenylthio refers to a phenylthio group substituted with up to three groups selected from halo, $(C_1-C_{10})$alkyl, halo$(C_1-C_7)$alkyl, hydroxy$(C_1-C_7)$alkyl, $(C_1-C_7)$alkoxy, halo$(C_1-C_7)$alkoxy, phenoxy, phenyl, $NO_2$, OH, CN, $(C_1-C_4)$alkanoyloxy, or benzyloxy.

As described in U.S. Pat. No. 5,145,843 the compounds of formula (1) may be made by condensing a compound of formula (3)

(3)

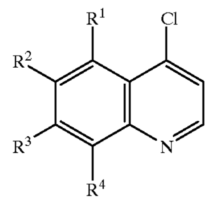

wherein $R^1$ to $R^4$ are as previously defined, with a compound of the formula (4)

HO—A (4)

wherein A is as previously defined. This reaction can be carried out neat, at a temperature in the range of 80–150° C., or preferably 130–140° C.

Many of the quinoline starting materials may be prepared as described in U.S. Pat. No. 5,145,843, and shown in the following reaction scheme below:

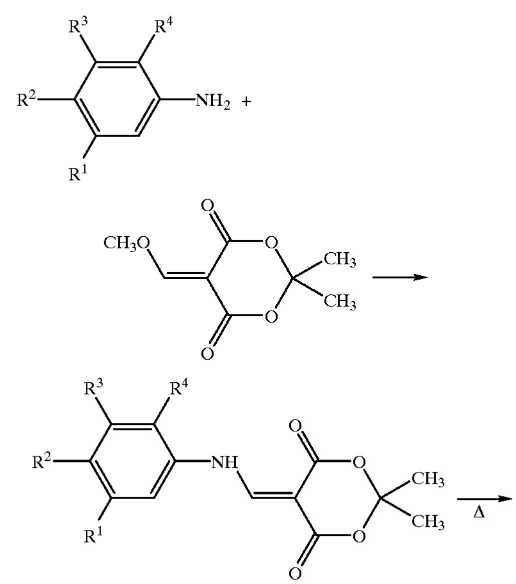

-continued

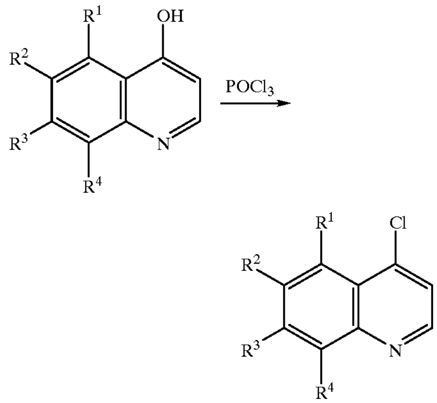

In cases where mixtures of isomeric products are obtained, the mixture of substituted 4-quinolines is chlorinated under standard conditions utilizing phosphorous oxychloride, and the isomeric 4-chloroquinolines are separated by liquid chromatography.

U.S. Pat. No. 5,245,036 describes an improvement over this process whereby the coupling step is carried out in the presence of a 4-dialkylaminopyridine catalyst.

Other known methods which may be used for preparing other types of quinoline materials are described as follows:

4-Hydroxyquinolines may be prepared via the Gould-Jacobs reaction of substituted anilines with ethoxymethylene diethylmalonate. *J.A.C.S.* 61, 2890 (1939). This procedure is also described in detail in *Organic Syntheses*, vol. 3 (1955), cited above in U.S. Pat. No. 5,145,843, for the preparation of 4,7-dichloroquinoline, which is a useful intermediate for the antimalarial drug chloroquin. Another general procedure is described in *Tetrahedron*, vol. 41, pp. 3033–3036 (1985).

Kokai Pat. No. Hei 1(1989)-246263 describes a method for producing 5,7-dichloro-4-(2-fluorophenoxy)-quinoline whereby a mixture of 3,5-dichloroaniline and Meldrum's acid is heated to give 4-oxo-5,7-dichloro-1,4-dihydroquinoline, which is reacted with phosphorus oxychloride to give 4,5,7-trichloroquinoline, which is then reacted with 2-fluorophenol to give the final compound.

Kokai Pat. No. Hei 5(1993)-1555856 describes an acrylic acid based route to produce an addition product with 3,5-dichloroaniline, which is then cyclized and oxidized to the corresponding quinoline compound.

*Tetrahedron Letters*, vol. 35, no. 32 (1994) describes a decarboxylation process to convert camptothecin, a compound which exhibits antineoplastic activity, to mappicine ketone, whose analogs are of interest in medicinal and pharmacological research. The conversion takes place upon extended reflux in DMF. Changing the solvent to triglyme at 200° C. gave a shorter reaction time. However, it is reported this reaction is limited to analogs with an intact a-hydroxylactone structure.

SUMMARY OF THE INVENTION

The present invention relates to a new improved, simplified process for the preparation of compounds of formula (1), whereby thionyl chloride is advantageously used as the chlorinating agent, to prepare the corresponding chloroquinoline intermediate prior to the final coupling reaction, and a single, inert high boiling polyether solvent is used throughout the entire reaction procedure. Such process is accomplished by:

a) reacting an aniline of formula (5), (5)

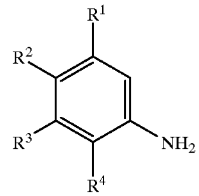

with an $(C_1–C_4)$alkoxymethylene malonate di$(C_1–C_4)$alkyl ester to obtain a compound of formula (7), wherein E is $(C_1–C_4)$alkyl, (7)

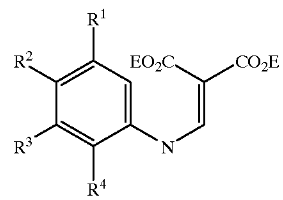

b) reacting the compound of formula (7) with application of heat to obtain an ester of formula (8), (8)

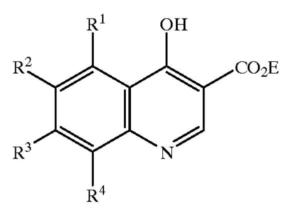

c) reacting the ester of formula (8) with a base selected from the group consisting of sodium carbonate, potassium carbonate, sodium hydroxide, and potassium hydroxide, to obtain a salt of formula (9), wherein M is Na or K, (9)

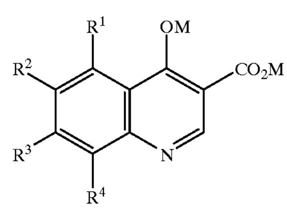

d) reacting the salt of formula (9) with a mineral acid selected from the group consisting of hydrochloric acid, sulfuric acid, and phosphoric acid, to obtain a 4-hydroxyquinoline acid of formula (10), (10)

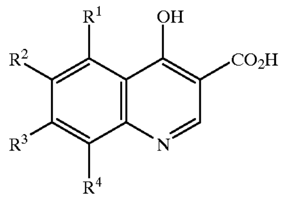

e) reacting the acid of formula (10) with the application of heat to obtain a 4-hydroxyquinoline of formula (11), (11)

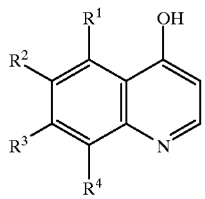

f) reacting the 4-hydroxyquinoline of formula (11) with thionyl chloride in the presence N,N-dimethylformamide or N,N-diethylformamide to obtain a 4-chloroquinoline of formula (12), (12)

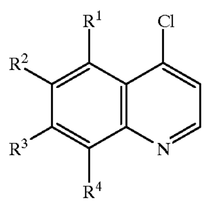

g) reacting the 4-chloroquinoline of formula (12) with a phenol of formula (13), (13)

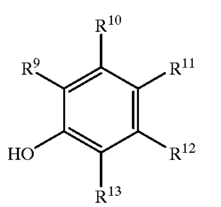

in the presence of a base selected from a group consisting of sodium carbonate, potassium carbonate, sodium hydroxide, and potassium hydroxide, to obtain a 4-oxysubstituted quinoline of formula (1).

DETAILED DESCRIPTION OF THE INVENTION

In the first step of the process, the aniline (5), wherein $R^1$–$R^4$ are as defined in formula (1), is reacted with an ($C_1$–$C_4$)alkoxymethylene malonate di($C_1$–$C_4$)alkyl ester (6), wherein E is ($C_1$–$C_4$)alkyl, or preferably, ethoxymethylene malonate diethyl ester (EMME), to give the adduct (7) with elimination of ethanol. This reaction occurs readily on heating these materials together in the absence of solvent or in the presence of an inert, high boiling solvent.

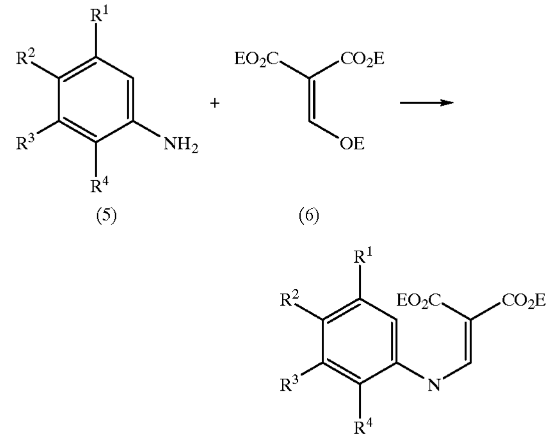

(5) (6)

(7)

Typically, a slight molar excess of the ($C_1$–$C_4$) alkoxymethylene malonate di ($C_1$–$C_4$) alkyl ester is used in the reaction. After about 30–60 minutes at a temperature of about 100–200° C., or more preferably, at about 150–170° C., the reaction is substantially complete. The alcohol produced in the reaction can be distilled off during the heating period. The temperature attained is limited by the presence of alcohol, and hence by its rate of removal.

In the next stage, the adduct (7), without isolation, is cyclized to the 4-hydroxyquinoline ester (8) by heating to a temperature of about 200–270° C. for a period of about 2–20 hours in the presence of an inert, high boiling solvent. As the reaction progresses, the insoluble ester precipitates.

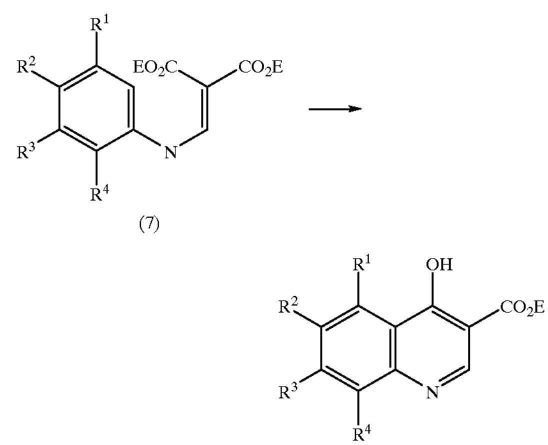

(7)

(8)

The ester (8) can be isolated at this stage and washed free of impurities, if desired, using the ethanol produced in the process, or washed with a low boiling hydrocarbon, such as, for example, hexane, and isolated. However, it is preferred to proceed directly to the next step without isolation of the ester.

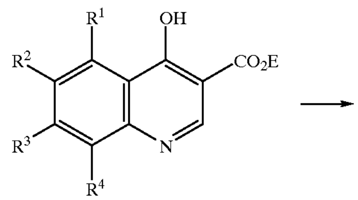

(8)

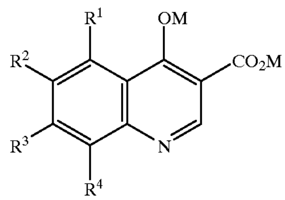

(9)

In the next step, the ester (8) is hydrolyzed by heating and reaction with about a 100 percent molar excess of an aqueous base, such as, for example, sodium carbonate, potassium carbonate, sodium hydroxide or potassium hydroxide, to obtain the disodium or dipotassium salt (9), wherein M is Na or K. A typical reaction time is about 1–5 hours at a temperature of about 50–110° C., or preferably 80–100° C.

The dipotassium or disodium salt (9) is then, typically without cooling, reacted with acid to precipitate the 4-hydroxyquinoline acid (10). The acidification is carried out by directly running the solution of the dipotassium or disodium salt into an aqueous solution of a mineral acid, such as, for example, hydrochloric acid, sulfuric acid, or phosphoric acid, at a temperature of about 40–110° C., or preferably 80–100° C. Carrying out the precipitation in this manner and preferably allowing for about a 30 minute post reaction digestion period at a temperature of about 80–105° C. has been found to produce acid (10) in a form that is particularly easy to filter after cooling the mixture.

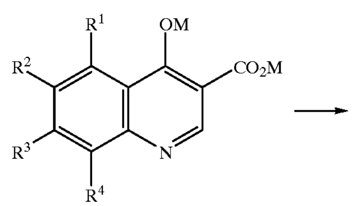

(9)

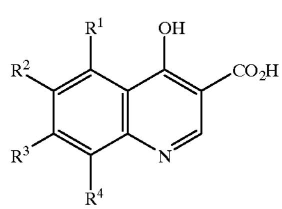

(10)

The acid may be washed with water before reslurrying in more solvent for the next reaction stage, which is the decarboxylation to the 4-hydroxyquinoline (11). It is not necessary to dry the acid separately since the water distills during the heat up and decarboxylation reaction. The reaction is run at a temperature of about 190–240° C., or preferably 210–230° C. for a period of about 2–5 hours, during which time, or subsequently, the more volatile components of the mixture are removed by distillation. This distillation creates the anhydrous conditions required for the next stage.

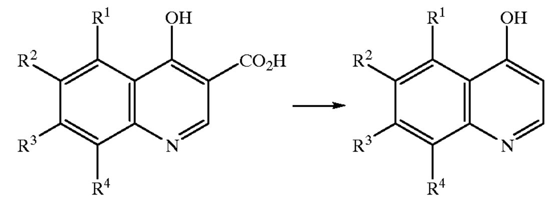

(10) (11)

In the next step, the reaction mixture is heated to a temperature of about 60–90° C., or preferably 60–80° C., in the presence of a catalytic amount (about 10 molar %) of N,N-dimethylformamide (DMF) or N,N-diethylformamide (DEF), and a 10–75% molar excess of thionyl chloride is added to obtain the 4-chloroquinoline (12) as its hydrochloride salt. The reaction is complete in about 3–4 hours. At the end of the reaction, the excess thionyl chloride and the sulfur dioxide are stripped from the mixture by distillation under reduced pressure at a temperature of about 60–95° C., or preferably 90–95° C.

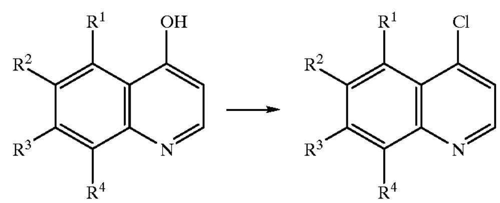

(11) (12)

In the final step, the 4-chloroquinoline, preferably without isolation, is coupled with the phenol (13). The product of the coupling is the desired quinoline of formula (1).

The reaction is carried out at a temperature of about 40–90° C., or preferably 45–50° C. in the presence of about an approximately equimolar amount of a phenol and about a 2.5 molar excess of an aqueous base, such as, for example, sodium carbonate, potassium carbonate, sodium hydroxide, or potassium hydroxide. Sodium hydroxide or potassium hydroxide is preferred, but sodium hydroxide gives a slower reaction. The speed of the reaction in either case is improved by distilling water from the reaction mixture as the reaction proceeds. Water enters the reaction with the base and is also formed by the reaction of the latter with the phenol. After removal of the water, the reaction is complete in about 2–3 hours.

The final product can be isolated from the final reaction by addition of water, followed by digestion at a temperature of about 40–95° C., or preferably 70–90° C for about 0–120 minutes, or preferably 30–60 minutes to insure dissolution of the inorganic salts, and then precipitation by cooling to room temperature, filtration or centrifugation, and washing with water.

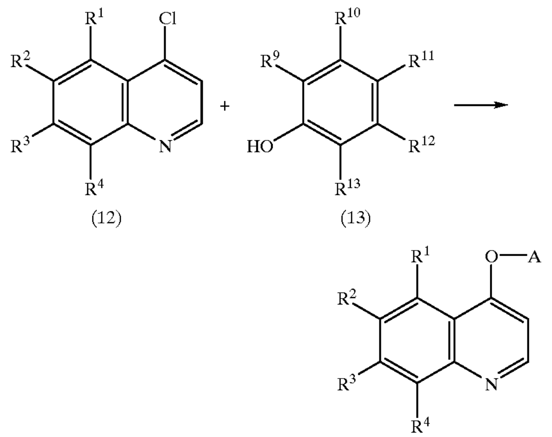

(12) (13)

(1)

Applicants have discovered the entire reaction sequence can advantageously be accomplished in a single, inert high boiling polyether solvent, such as, for example, diethylene glycol dimethyl ether, triethylene glycol dimethyl ether, triethylene glycol diethyl ether, or tetraethylene glycol dimethyl ether. When a single solvent of this type is used, tetraethylene glycol dimethyl ether, which is also known as tetraglyme, is often preferred. It has been found to be highly preferable to control the water:solvent ratio throughout the reaction sequence for optimal purity and/or recovery of the product of each reaction step. A ratio of about 0.5:1 to 1.5:1 of water:solvent is preferred.

The following example further illustrates the present invention. It should not be construed as limiting the invention in any manner.

Preparation of 5,7-dichloro-4-(4-fluorophenoxy) quinoline: In a 500 ml three-neck, mechanically stirred round bottom flask, equipped with a short path distillation head, 3,5-dichloroaniline (24.4 gm, 0.15 moles), ethoxymethylene malonate diethyl ester (EMME, 34.15 gm, 0.158 moles), and tetraethylene glycol dimethyl ether (tetraglyme, 202.2 gm) were mixed. While sweeping the head space with nitrogen, the reaction solution was heated to about 160° C. Ethanol was distilled as it was formed during the reaction. After about 40 minutes at this temperature, conversion to the EMME adduct was greater than 98%. The resulting homogenous solution was heated to about 230° C. while maintaining a head space sweep of nitrogen. As the reaction progressed, the insoluble product, 5,7-dichloro-3-carboethoxy-4-hydroxyquinbline (DCHQ ester) precipitated. After 5.5 hours, the conversion from the EMME adduct to the DCHQ ester was complete as no EMME adduct was detected by HPLC. The reaction mixture was allowed to cool to room temperature.

The resulting DCHQ ester slurry was heated to about 90° C., and a solution containing 20.37 gm of 86.4% potassium hydroxide (0.314 moles) and 71.6 gm of water was added. After a short while, the reaction mixture became a homogenous solution. The solution was heated to a temperature of about at 90° C. until the conversion of DCHQ ester to the dipotassium salt of 5,7-dichloro-4-hydroxyquinoline-3-carboxylic acid (DCHQ acid) was over 99% complete. Without cooling, the hydrolysate solution was added to a solution containing of 19.45% hydrochloric acid (63.8 gm, 0.34 moles). The addition was done over about a 1.5 hour period. The resulting mixture was heated to a temperature of about 90° C. for an additional period of approximately one hour.

After allowing the mixture to cool to room temperature, the solids were isolated by filtration and washed three times with 45 ml of water. The cake was dried at a temperature of about 80° C. and a pressure of about 50 mm Hg for about four hours resulting in 35.4 gm of light tan powder. The yield and purity of the DCHQ acid was 91.5% and 100%, respectively.

In a mechanically stirred 500 ml three neck round bottom flask equipped with a distillation head, DCHQ acid (35.3 gm, 0.137 moles) and tetraglyme (195.6 gm) were mixed. To simulate a wet cake, 8.9 gm of water was added. The reaction mixture was heated from room temperature to a temperature of about 215° C. over about a two hour period. The reaction mixture was then heated to a temperature of about 225–230° C. for about three hours. After about 2.75 hours, the conversion was greater than 99% by HPLC. The reaction mixture was cooled to a temperature of about 170° C. and the pressure was slowly adjusted to about 22 mm Hg. The distillation was continued until a head temperature of about 150–155° C. was reached. After cooling to room temperature, the amount of tetraglyme removed during the drying step was added to the reactor (12.4 gm).

After heating the reaction mixture to a temperature of about 70° C., N,N-dimethylformamide (DMF, 1.0 gm, 0.0137 moles) and thionyl chloride (20.5 gm, 0.172 moles) were added. The reaction mixture was heated to a temperature of about 75–80° C. for about 2.5 hours. After about two hours, conversion was greater than 98% by HPLC. The pressure was slowly reduced from ambient to about 15 mm Hg followed by gradual heating to a temperature of about 90–95° C. After about 45 minutes at those conditions, the temperature was adjusted to about 50° C. and the vacuum was released.

While holding at a temperature of about 50° C., 4-fluorophenol (PFP, 17.0 gm, 0.152 moles) was added to the mixture. After stirring for about five minutes, 43% potassium hydroxide (KOH, 40.9 gm, 0.316 moles) was added in four shots keeping the temperature below about 60° C. After the addition was complete, the pressure was carefully reduced to about 15 mm Hg. The system was heated to a temperature of about 45–50° C. for about two hours. The conversion was found to be greater than 97% by HPLC. The vacuum was released and 195 gm of water was added. The temperature was then slowly raised to about 80° C. and held there for about 30 minutes. The heat was turned off and the reaction mixture was allowed to cool slowly to room temperature. The solids were isolated by filtration. The solids were washed three times with 70 ml of water. The filter cake was dried at about 80° C. and a pressure of about 50 mm Hg for about 3.5 hours resulting in 37.5 gm of tan solid. Purity was found to be 100% and 99.8% by internal standard GC and HPLC, respectively. Yield for 5,7-dichloro-4-(4-fluorophenoxy)quinoline was 88.7% from DCHQ acid and 81.2% from DCA.

What is claimed is:

1. A process for preparing 4-oxysubstituted quinolines of formula (1)

(1)

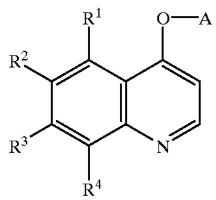

wherein $R^1$ and $R^3$ are independently halo and $R^2$ and $R^4$ are H; or $R^3$ is halo, $R^1$ is halo or H, and $R^2$ and $R^4$ are H; or $R^4$ is halo and $R^1$ to $R^3$ are H;

A is a phenyl group of formula (2)

(2)

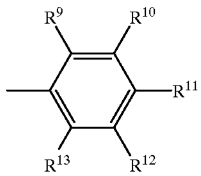

wherein $R^9$ to $R^{13}$ are independently H, CN, $NO_2$, OH, halo, $(C_1–C_4)$alkyl, $(C_2–C_4)$alkanoyl, halo$(C_1–C_7)$alkyl, hydroxy$(C_1–C_7)$alkyl, $(C_1–C_7)$alkoxy, halo$(C_1–C_7)$alkoxy, $(C_1–C_7)$alkylthio, halo$(C_1–C_7)$alkylthio, phenyl, substituted phenyl, phenoxy, substituted phenoxy, phenylthio, substituted phenylthio, phenyl$(C_1–C_4)$alkyl, substituted phenyl$(C_1–C_4)$alkyl, benzoyl, $SiR^{20}R^{21}R^{22}$, or $OSiR^{20}R^{21}R^{22}$ where $R^{20}$, $R^{21}$, and $R^{22}$ are H, a $(C_1–C_6)$alkyl group, phenyl, or substituted phenyl, provided that at least one of $R^{20}$, $R^{21}$, and $R^{22}$ is other than H, or $R^{11}$ and $R^{12}$ or $R^{12}$ and $R^{13}$ combine to form a carbocyclic ring, and provided that unless all of $R^9$ to $R^{13}$ are H or F, then at least two of $R^9$ to $R^{13}$ are H;

which comprises:

a) reacting an aniline of formula (5), (5)

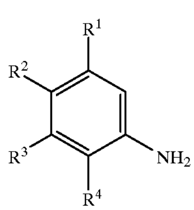

with an $(C_1–C_4)$alkoxymethylene malonate di$(C_1–C_4)$alkyl ester to obtain a compound of formula (7), wherein E is $(C_1–C_4)$alkyl, (7)

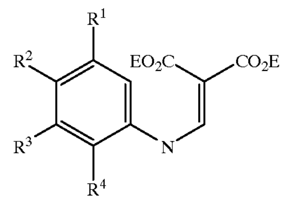

b) reacting the compound of formula (7) with application of heat to obtain an ester of formula (8), (8)

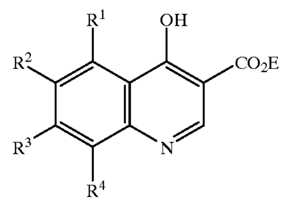

c) reacting the ester of formula (8) with a base selected from the group consisting of sodium carbonate, potassium carbonate, sodium hydroxide, and potassium hydroxide, to obtain a salt of formula (9), wherein M is Na or K, (9)

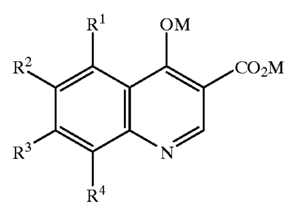

d) reacting the salt of formula (9) with a mineral acid selected from the group consisting of hydrochloric acid, sulfuric acid, and phosphoric acid, to obtain a 4-hydroxyquinoline acid of formula (10), (10)

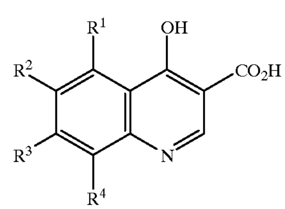

e) reacting the acid of formula (10) with the application of heat to obtain a 4-hydroxyquinoline of formula (11), (11)

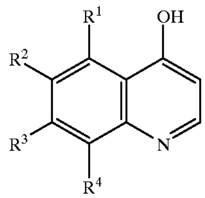

f) reacting the 4-hydroxyquinoline of formula (11) with thionyl chloride in the presence N,N-dimethylformamide or N,N-diethylformamide to obtain a 4-chloroquinoline of formula (12), (12)

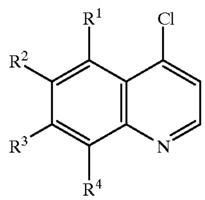

g) reacting the 4-chloroquinoline of formula (12) with a phenol of formula (13), (13)

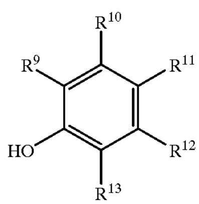

in the presence of a base selected from a group consisting of sodium carbonate, potassium carbonate, sodium hydroxide, and potassium hydroxide, to obtain a 4-oxysubstituted quinoline of formula (1)

wherein the entire reaction sequence a)–g) is carried out in the presence of a single, inert high boiling polyether solvent.

2. The process of claim 1, wherein the single, inert high boiling polyether solvent is selected from the group consisting of diethylene glycol dimethyl ether, triethylene glycol dimethyl ether, triethylene glycol diethyl ether, and tetraethylene glycol dimethyl ether.

3. The process of claim 2 wherein the inert, high boiling polyether solvent is tetraethylene glycol dimethyl ether.

4. A process for preparing 5,7-dichloro-4-(4-fluorophenoxy)quinoline which comprises:

a) reacting 3,5-dichloroaniline with an ($C_1$–$C_4$) alkyloxymethylene malonate diethyl ester to obtain an adduct, b) heating the adduct to obtain 5,7-dichloro-3-carboethoxy-4-hydroxyquinoline, c) reacting 5,7-dichloro-3-carboethoxy-4-hydroxyquinoline with a base selected from the group consisting of sodium carbonate, potassium carbonate, sodium hydroxide, and potassium hydroxide, to obtain a salt of 5,7-dichloro-4-hydroxyquinoline-3-carboxylic acid, d) reacting the salt of 5,7-dichloro-4-hydroxyquinoline-3-carboxylic acid with a mineral acid selected from the group consisting of hydrochloric acid, sulfuric acid, and phosphoric acid, to obtain 5,7-dichloro-4-hydoxyquinoline-3-carboxylic acid, e) heating 5,7-dichloro-4-hydoxyquinoline-3-carboxylic acid to obtain 5,7-dichloro-4-hydoxyquinoline, f) reacting 5,7-dichloro-4-hydoxyquinoline with thionyl chloride in the presence of N,N-dimethylformamide or N,N-diethylformamide to obtain 4,5,7-trichloroquinoline, g) reacting 4,5,7-trichloroquinoline with 4-fluorophenol in the presence of a base selected from the group consisting of sodium carbonate, potassium carbonate, sodium hydroxide, and potassium hydroxide, to obtain 5,7-dichloro-4-(4-fluorophenoxy)quinoline wherein the reaction sequence is carried out in a single, inert high boiling polyether solvent.

5. The process of claim 4 wherein the single, inert high boiling polyether solvent is selected from the group consisting dimethylene glycol diethyl ether, triethylene glycol dimethyl ether, triethylene glycol diethyl ether, and tetraethylene glycol dimethyl ether.

6. The process of claim 5 wherein the inert, high boiling polyether solvent is tetraethylene glycol dimethyl ether.

* * * * *